(12) United States Patent
Kono et al.

(10) Patent No.: US 11,038,201 B2
(45) Date of Patent: Jun. 15, 2021

(54) ADDITIVE FOR NONAQUEOUS ELECTROLYTE SOLUTIONS, NONAQUEOUS ELECTROLYTE SOLUTION, AND ELECTRICITY STORAGE DEVICE

(71) Applicant: SUMITOMO SEIKA CHEMICALS CO., LTD., Hyogo (JP)

(72) Inventors: Yuki Kono, Hyogo (JP); Shohei Fujimoto, Hyogo (JP); Koji Fujita, Hyogo (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 262 days.

(21) Appl. No.: 15/758,241

(22) PCT Filed: Sep. 8, 2016

(86) PCT No.: PCT/JP2016/076455
§ 371 (c)(1),
(2) Date: Mar. 7, 2018

(87) PCT Pub. No.: WO2017/043576
PCT Pub. Date: Mar. 16, 2017

(65) Prior Publication Data
US 2018/0248226 A1     Aug. 30, 2018

(30) Foreign Application Priority Data

Sep. 9, 2015  (JP) .............................. JP2015-177528

(51) Int. Cl.

| | |
|---|---|
| *H01M 10/0567* | (2010.01) |
| *H01G 11/64* | (2013.01) |
| *H01M 10/0569* | (2010.01) |
| *H01M 10/052* | (2010.01) |
| *C07D 327/04* | (2006.01) |
| *C07D 333/48* | (2006.01) |
| *H01G 11/06* | (2013.01) |
| *H01G 11/60* | (2013.01) |
| *H01G 11/62* | (2013.01) |
| *H01M 10/0525* | (2010.01) |
| *H01M 10/0568* | (2010.01) |

(52) U.S. Cl.
CPC ...... *H01M 10/0567* (2013.01); *C07D 327/04* (2013.01); *C07D 333/48* (2013.01); *H01G 11/06* (2013.01); *H01G 11/60* (2013.01); *H01G 11/62* (2013.01); *H01G 11/64* (2013.01); *H01M 10/052* (2013.01); *H01M 10/0525* (2013.01); *H01M 10/0568* (2013.01); *H01M 10/0569* (2013.01); *H01M 2220/30* (2013.01); *H01M 2300/0037* (2013.01); *Y02E 60/13* (2013.01)

(58) Field of Classification Search
CPC ......... H01M 10/0567; H01M 10/0569; H01M 10/0568; H01M 10/0525; H01M 10/052; H01M 2220/30; H01M 2300/0037; Y02E 60/13; H01G 11/64; H01G 11/06; H01G 11/60; H01G 11/62; C07D 327/04; C07D 333/48

See application file for complete search history.

(56) References Cited

U.S. PATENT DOCUMENTS

| | | | | |
|---|---|---|---|---|
| 2,449,173 | A | * | 9/1948 | Morris ................ C07D 333/48 549/66 |
| 2,810,728 | A | | 10/1957 | Beesley |
| 2006/0110677 | A1 | * | 5/2006 | Houlihan ............. G03F 7/0397 430/270.1 |
| 2013/0196952 | A1 | * | 8/2013 | Bunnage ............. C07D 451/02 514/89 |
| 2014/0213689 | A1 | * | 7/2014 | Leplianin ............... C08L 35/04 523/118 |

(Continued)

FOREIGN PATENT DOCUMENTS

| | | |
|---|---|---|
| CN | 103493280 | 1/2014 |
| CN | 104508896 | 4/2015 |

(Continued)

OTHER PUBLICATIONS

Scifinder Reaction for Bunnage reference above Aug. 2013.*

(Continued)

*Primary Examiner* — Laura Weiner
(74) *Attorney, Agent, or Firm* — Hamre, Schumann, Mueller & Larson, P.C.

(57) ABSTRACT

Disclosed is an additive for non-aqueous electrolyte solutions, which include a compound represented by Formula (1).

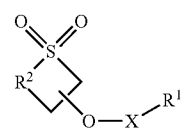

(1)

In Formula (1), X represents a sulfonyl group or a carbonyl group, $R^1$ represents an alkyl group having 1 to 4 carbon atoms which may be substituted with a halogen atom, or the like, and $R^2$ represents a divalent hydrocarbon group having 1 to 3 carbon atoms which may be substituted with a halogen atom, or represents a divalent group formed of a divalent hydrocarbon group having 1 to 3 carbon atoms which may be substituted with a halogen atom, and an oxygen atom that constitutes a cyclic structure together with the hydrocarbon group.

7 Claims, 1 Drawing Sheet

(56) References Cited

U.S. PATENT DOCUMENTS

2015/0221985 A1* 8/2015 Abe .................. H01M 10/0567
429/329

FOREIGN PATENT DOCUMENTS

| | | | |
|---|---|---|---|
| CN | 104584311 | | 4/2015 |
| EP | 2 755 272 | | 7/2014 |
| JP | 63-102173 | | 5/1988 |
| JP | 2012-056925 | * | 3/2012 |
| WO | WO 2014/021272 | * | 2/2014 |

OTHER PUBLICATIONS

Vorob'eva, et al., "Copolymerization of N-vinylpyrrolidone with 3-methacryloyloxytetrahydrothiophene1,1' Dioxide", Russian Journal of Applied Chemistry vol. 79, No. 6, 2006, pp. 997-1000, XP019406787.

Bezmenova, et al., "Behavior of Sulfolane Derivatives in the Friedel—Crafts Reaction", Chemistry of Heterocyclic Compounds, Kluwer Academic Publishers—Plenum Publishers, New York, vol. 7, 1971, pp. 1378-1380, XP000602736.

Supplementary Partial Search Report issued in counterpart European Patent Application No. 16844437.0, Jan. 9, 2019, 12 pages.

Office Action issued in counterpart Japanese Application No. 2017-539216, dated Oct. 30, 2018, 3 pages.

Chung, et al., "Origin of Graphite Exfoliation—An Investigation of the Important Role of Solvent Cointercalation", Journal of the Electrochemical Society, 147 (12), 2000, pp. 4391-4398.

International Preliminary Report on Patentability issued in International Application No. PCT/JP2016/076455, dated Mar. 22, 2018, 6 pages.

International Search Report issued in International Application No. PCT/JP2016/076455, dated Oct. 5, 2016, 2 pages.

* cited by examiner

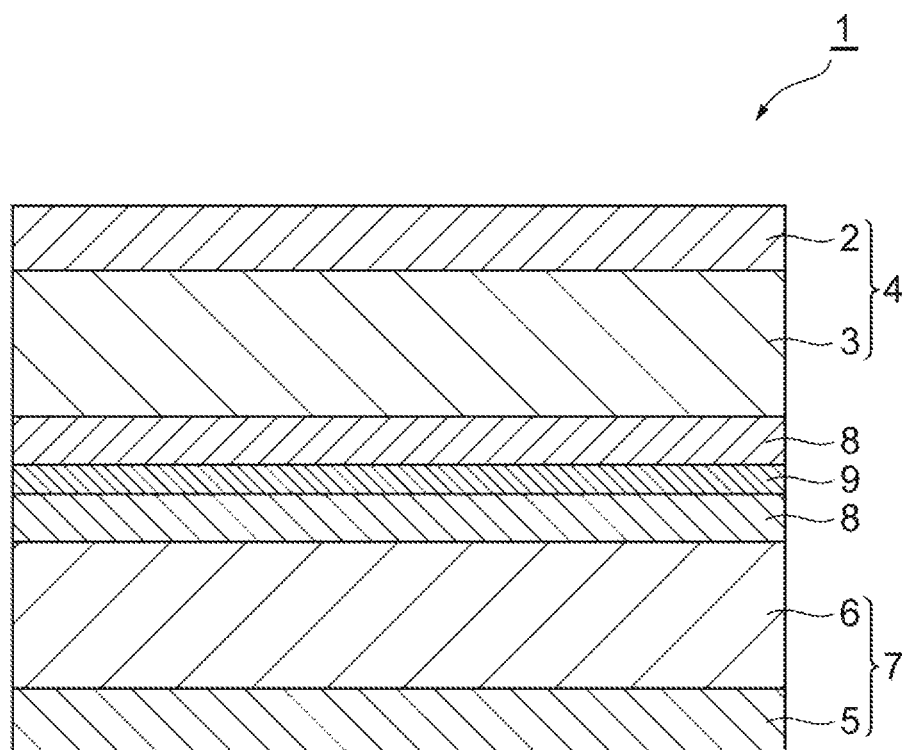

ADDITIVE FOR NONAQUEOUS ELECTROLYTE SOLUTIONS, NONAQUEOUS ELECTROLYTE SOLUTION, AND ELECTRICITY STORAGE DEVICE

TECHNICAL FIELD

The present invention relates to an additive for non-aqueous electrolyte solutions, a non-aqueous electrolyte solution, and a power storage device.

BACKGROUND ART

In recent years, along with an increase in attention to solving environmental problems and establishing a sustainable recycling-based society, non-aqueous electrolyte solution secondary batteries typified by lithium ion batteries have been widely studied. The lithium ion batteries are used as power sources for laptops, mobile phones, and the like from the viewpoint that they have high working voltages and energy densities. The lithium ion batteries are expected to realize a higher capacity of batteries from the viewpoint that they have higher energy densities than lead batteries and nickel-cadmium batteries.

However, the lithium ion batteries have a problem in that the capacity of the batteries decreases over time in charge/discharge cycles. One factor contributing to the decrease in the capacity is considered to be, for example, that charge/discharge cycles over a long period of time cause occurrence of the decomposition of an electrolyte solution due to electrode reactions, a reduction in impregnation of an electrolyte into an electrode active material layer, and a reduction in the intercalation efficiency of lithium ions.

As a method for suppressing a reduction in the capacity of batteries due to charge/discharge cycles, a method in which various additives are added to an electrolyte solution have been examined. The additives are generally decomposed during the initial charge and discharge to form a film called a solid electrolyte interface (SEI) on the surface of an electrode. Since the SEI is formed during the initial charge/discharge cycle, electricity is suppressed from being consumed for the decomposition of the electrolyte solution in the later charge/discharge, and lithium ions can be transferred between electrodes through the SEI. That is, the formation of an SEI is considered to suppress the deterioration of secondary batteries during the repeating charge/discharge cycles, and make a great contribution to an improvement in battery characteristics, storage characteristics, load characteristics, and the like.

As an additive for an electrolyte solutions, for example, Patent Literatures 1 to 3 disclose cyclic monosulfonic acid esters, Patent Literature 4 discloses a sulfur-containing aromatic compound, Patent Literature 5 discloses a disulfide compound, and Patent Literatures 6 to 9 disclose disulfonic acid esters, respectively. In addition, Patent Literatures 10 to 15 each disclose an electrolyte solution containing a cyclic carboxylic acid ester or a cyclic sulfone.

CITATION LIST

Patent Literature

[Patent Literature 1] Japanese Unexamined Patent Publication No. S63-102173
[Patent Literature 2] Japanese Unexamined Patent Publication No. 2000-003724
[Patent Literature 3] Japanese Unexamined Patent Publication No. H11-339850
[Patent Literature 4] Japanese Unexamined Patent Publication No. II05-258753
[Patent Literature 5] Japanese Unexamined Patent Publication No. 2001-052735
[Patent Literature 6] Japanese Unexamined Patent Publication No. 2009-038018
[Patent Literature 7] Japanese Unexamined Patent Publication No. 2005-203341
[Patent Literature 8] Japanese Unexamined Patent Publication No. 2004-281325
[Patent Literature 9] Japanese Unexamined Patent Publication No. 2005-228631
[Patent Literature 10] Japanese Unexamined Patent Publication No. H04-87156
[Patent Literature 11] Japanese Unexamined Patent Publication No. H10-50342
[Patent Literature 12] Japanese Unexamined Patent Publication No. H08-45545
[Patent Literature 13] Japanese Unexamined Patent Publication No. 2001-6729
[Patent Literature 14] Japanese Unexamined Patent Publication No. S63-102173
[Patent Literature 15] Japanese Unexamined Patent Publication No. H05-074486

Non Patent Literature

[Non-Patent Literature 1] Geun-Chang, Hyung-Jin kim, Seung-II Yu, Song-Hui Jun, Jong-Wook Choi, Myung-Hwan Kim. Journal of The Electrochemical Society, 147, 12, 4391 (2000)

SUMMARY OF INVENTION

Technical Problem

A compound having low lowest unoccupied molecular orbital (LUMO) energy is an excellent electron receptor, and is said to be able to form a stable SEI on the surface of an electrode of a non-aqueous electrolyte solution secondary battery or the like (for example, Non-Patent Literature 1). Some of the additives in the related art, such as the compounds disclosed in Patent Literatures 1 to 9, exhibit low LUMO energy, but have a problem in that they are chemically unstable and easily deteriorated by the effects of moisture and temperature. For example, disulfonic acid esters exhibit low LUMO energy, but are unstable to moisture and easily deteriorated. Therefore, in a case where the disulfonic acid esters are stored for a long period of time, they require tight control of the moisture content and the temperature. Generally, heat-resistant temperatures of about 60° C. and about 80° C. are generally required for a lithium ion battery and a lithium ion capacitor, respectively, and thus an improvement in the high-temperature stability of an additive for non-aqueous electrolyte solutions used in a power storage device has been one of important issues.

Furthermore, in a case of an electrolyte solution containing an additive in the related art, the battery characteristics of a power storage device are easily deteriorated during the use of the electricity storage device for a long period of time in the repeating charge/discharge cycles, and therefore, a further improvement in the cycle characteristics has been required.

The electrolyte solutions described in Patent Literatures 10 to 14 can suppress an irreversible reduction in the capacity to some degrees with an SEI produced on the surface of a negative electrode through electrochemical reduction decomposition. However, although the SEI formed from such additives in these electrolyte solutions was excellent in performance for protection of electrodes, it was not sufficient in the strength to withstand long-term use. As a result, it had problems in that, for example, the SEI is decomposed during the use of a power storage device or cracks are generated in the SEI, causing exposure of the surface of the negative electrode, and generation of the decomposition of the electrolyte solution occurs, leading to a reduction in battery characteristics. An electrolyte solution in which the ethylene carbonate-based compound described in Patent Literature 15 is used as an additive had a problem such as generation of gas including carbon dioxide during the decomposition of ethylene carbonate on the electrode, which leads to a reduction in battery performance. Generation of the gas is noticeable, particularly in the repeating charge/discharge cycles at a high temperature or in a long period of time.

As described above, there has been a room for a further improvement in storage stability, cycle characteristics for maintaining performance in the repeating charge/discharge cycles, or suppression of gas generation, for an additive for non-aqueous electrolyte solutions.

Therefore, a main object of the invention is to provide an additive for non-aqueous electrolyte solutions, which has high storage stability and is capable of improving cycle characteristics and suppressing gas generation for a power storage device.

Solution to Problem

The present inventors have found that a compound including a specific partial structure exhibits low LUMO energy and is chemically stable. In addition, the present inventors have found that in a case where such a compound is used as an additive for non-aqueous electrolyte solutions in a power storage device such as a non-aqueous electrolyte solution secondary battery, excellent cycle characteristics are obtained and generation of gas is suppressed, leading to the completion of the invention.

That is, in an aspect of the invention, an additive for non-aqueous electrolyte solutions, including a compound represented by Formula (1), is provided.

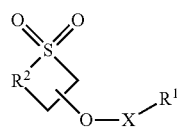
(1)

In Formula (1), X represents a sulfonyl group or a carbonyl group, $R^1$ represents an alkyl group having 1 to 4 carbon atoms which may be substituted with a halogen atom, an alkenyl group having 2 to 4 carbon atoms which may be substituted with a halogen atom, an alkynyl group having 2 to 4 carbon atoms which may be substituted with a halogen atom, an aryl group which may be substituted with a halogen atom, an alkoxy group having 1 to 4 carbon atoms which may be substituted with a halogen atom, an alkenyloxy group having 2 to 4 carbon atoms which may be substituted with a halogen atom, an alkynyloxy group having 2 to 4 carbon atoms which may be substituted with a halogen atom, or an aryloxy group which may be substituted with a halogen atom. $R^2$ represents a divalent hydrocarbon group having 1 to 3 carbon atoms which may be substituted with a halogen atom, or a divalent group formed of a divalent hydrocarbon group having 1 to 3 carbon atoms which may be substituted with a halogen atom, and an oxygen atom that constitutes a cyclic structure together with the hydrocarbon group.

Here, "which may be substituted with a halogen atom" as used in the specification denotes that a hydrogen atom included in each of groups may be substituted with a halogen atom.

The compound represented by Formula (1) is a cyclic sulfone compound. It is considered that the cyclic sulfone compound can cause a ring-opening polymerization, which leads to formation of a rigid SEI. Further, the compound of the invention, which contains a carbonyloxy group or sulfonyloxy group bonded to a ring, is considered to exhibit low LUMO energy and exert excellent ion conductivity. Therefore, the compound is considered to be capable of forming a stable SEI which withstands a long-term use.

Advantageous Effects of Invention

According to the invention, an additive for non-aqueous electrolyte solutions, which has high storage stability and is capable of improving cycle characteristics, and suppression of gas generation for a power storage device, is provided. In a case of being used in a power storage device such as a non-aqueous electrolyte solution secondary battery and an electric double layer capacitor, the additives for a non-aqueous electrolyte solution according to some embodiments can form a stable solid electrolyte interface (SEI) on the surface of an electrode to improve battery characteristics such as cycle characteristics, a charge/discharge capacity, and internal resistance.

BRIEF DESCRIPTION OF DRAWINGS

FIG. 1 is a cross-sectional view showing an embodiment of a power storage device.

DESCRIPTION OF EMBODIMENTS

Hereinafter, suitable embodiments of the invention will be described in detail. However, the invention is not limited to the following embodiments.

An additive for non-aqueous electrolyte solutions according to the present embodiment includes one kind, or two or more kinds of compounds represented by Formula (1).

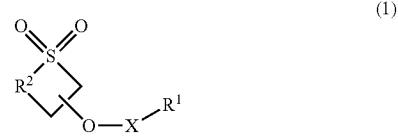
(1)

In Formula (1), X represents a sulfonyl group or a carbonyl group, $R^1$ represents an alkyl group having 1 to 4 carbon atoms which may be substituted with a halogen atom, an alkenyl group having 2 to 4 carbon atoms which may be substituted with a halogen atom, an alkynyl group having 2 to 4 carbon atoms which may be substituted with a halogen atom, an aryl group which may be substituted with a halogen atom, an alkoxy group having 1 to 4 carbon atoms which may be substituted with a halogen atom, an alkenyloxy group having 2 to 4 carbon atoms which may be substituted with a halogen atom, an alkynyloxy group having 2 to 4 carbon atoms which may be substituted with a halogen atom, or an aryloxy group which may be substituted with a halogen atom. $R^2$ represents a divalent hydrocarbon group having 1 to 3 carbon atoms which may be substituted with a halogen atom, or a divalent group formed of a divalent hydrocarbon group having 1 to 3 carbon atoms which may be substituted with a halogen atom, and an oxygen atom that constitutes a cyclic structure together with the hydrocarbon group.

$R^2$ in Formula (1) may be an alkylene group having 1 to 3 carbon atoms which is substituted with a halogen atom, or an oxyalkylene group having 1 to 3 carbon atoms which may be substituted with a halogen atom. An oxygen atom in the oxyalkylene group may be bonded to a sulfone group in Formula (1). A hydrocarbon group (particularly an alkylene group) contained in $R^2$ may have 1 or 2 carbon atoms. Specific examples of $R^2$ include —$CH_2$—, —$CH_2CH_2$—, —$CH_2CH_2CH_2$—, —CFHCH$_2$—, —$CF_2CH_2$—, —$OCH_2$—, and —$OCH_2CH_2$—, As shown in Formula (1)', a carbonyloxy group or a sulfonyloxy group may be bonded to the third position of a cyclic sulfone. This compound tends to exhibit particularly low LUMO energy and exert superior ion conductivity.

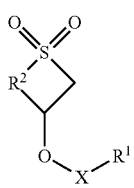

(1)'

From the viewpoint that the battery resistance is easily further lowered, the compound of Formula (1) may be a compound represented by Formula (1a) or (1b).

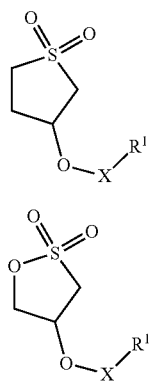

(1a)

(1b)

In Formulae (1a) and (1b), X and $R^1$ have the same definitions as X and $R^1$ in Formula (1), respectively.

From the viewpoints that the battery resistance is lower and the generation of gases is further suppressed, X in Formulae (1), (1a), and (1b) may be a sulfonyl group.

From the viewpoint that the battery resistance is further lowered, $R^1$ in Formulae (1), (1a), and (1b) may be an alkyl group having 1 to 4 carbon atoms which may be substituted with a halogen atom, an alkynyl group having 2 to 4 carbon atoms which may be substituted with a halogen atom, an aryl group which may be substituted with a halogen atom, an alkoxy group having 1 to 4 carbon atoms which may be substituted with a halogen atom, an alkynyloxy group having 2 to 4 carbon atoms which may be substituted with a halogen atom, or an aryloxy group which may be substituted with a halogen atom.

$R^1$ in formulae (1), (1a), and (1b) may be, from the viewpoint that the compounds represented by these formulae containing a group having an unsaturated bond form a more rigid SEI, an alkenyl group having 2 to 4 carbon atoms which may be substituted with a halogen atom, an alkynyl group having 2 to 4 carbon atoms which may be substituted with a halogen atom, an aryl group which may be substituted with a halogen atom, an alkenyloxy group having 2 to 4 carbon atoms which may be substituted with a halogen atom, an alkynyloxy group having 2 to 4 carbon atoms which may be substituted with a halogen atom, or an aryloxy group which may be substituted with a halogen atom.

$R^1$ in the formulae (1), (1a), and (1b) may be, from the viewpoint that the compounds represented by these formulae exert superior ion conductivity, an alkyl group having 1 to 4 carbon atoms which may be substituted with a halogen atom, an alkoxy group having 1 to 4 carbon atoms which may be substituted with a halogen atom, an alkenyloxy group having 2 to 4 carbon atoms which may be substituted with a halogen atom, an alkynyloxy group having 2 to 4 carbon atoms which may be substituted with a halogen atom, or an aryloxy group which may be substituted with a halogen atom.

Examples of the alkyl group having 1 to 4 carbon atoms which may be substituted with a halogen atom, include a methyl group, an ethyl group, an n-propyl group, an isopropyl group, an n-butyl group, an isobutyl group, and a t-butyl group. As the alkyl group having 1 to 4 carbon atoms, a methyl group can be selected.

Examples of the alkenyl group having 2 to 4 carbon atoms which may be substituted with a halogen atom, include a vinyl group, an allyl group, an isopropenyl group, a 1-butenyl group, a 2-butenyl group, a 3-butenyl group, an isobutenyl group, and a 1,1-difluoro-1-propenyl group. As the alkenyl group having 2 to 4 carbon atoms, an allyl group which may be substituted with a halogen atom can be selected.

Examples of the alkynyl group having 2 to 4 carbon atoms which may be substituted with a halogen atom, include a 1-propynyl group, a 2-propynyl group, a 1-butynyl group, a 2-butynyl group, and a 3-butynyl group. As the alkynyl group having 2 to 4 carbon atoms, a 2-propynyl group which may be substituted with a halogen atom can be selected.

Examples of the aryl group which may be substituted with a halogen atom include a phenyl group, a tolyl group, a xylyl group, and a naphthyl group.

Examples of the alkoxy group having 1 to 4 carbon atoms which may be substituted with a halogen atom, include a methoxy group, an ethoxy group, an n-propoxy group, and an n-butoxy group.

Examples of the aryloxy group which may be substituted with a halogen atom include a phenoxy group, a 2-methylphenoxy group, a 3-methylphenoxy group, a 4-methylphenoxy group, a 2-ethylphenoxy group, a 3-ethylphenoxy group, a 4-ethylphenoxy group, a 2-methoxyphenoxy group, a 3-methoxyphenoxy group, and a 4-methoxyphenoxy group.

Examples of the alkenyloxy group having 2 to 4 carbon atoms which may be substituted with a halogen atom, include a 2-propenyloxy group, a 1-methyl-2-propenyloxy group, a 2-methyl-2-propenyloxy group, a 2-butenyloxy group, and a 3-butenyloxy group.

Examples of the alkynyloxy group having 2 to 4 carbon atoms which may be substituted with a halogen atom, include a 2-propynyloxy group, a 1-methyl-2-propynyloxy group, a 2-methyl-2-propynyloxy group, a 2-butynyloxy group, and a 3-butynyloxy group.

Examples of the halogen atom include an iodine atom, a bromine atom, and a fluorine atom. From the viewpoint that the battery resistance can be easily lowered, as the halogen atom, a fluorine atom can be selected.

Examples of the compound represented by Formula (1) include a compound represented by Formula (2), (3), (4), (5), (6), (7), (8), (9), (10), (11), (12), (13), (14), or (15).

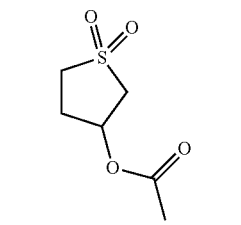
(2)

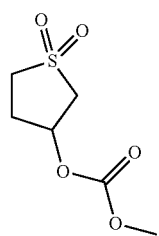
(3)

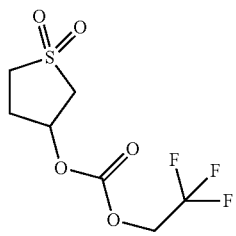
(4)

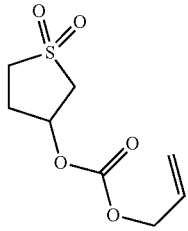
(5)

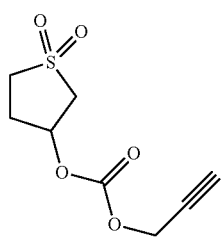
(6)

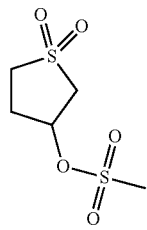
(7)

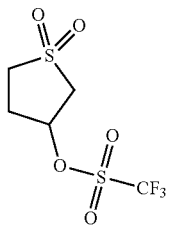
(8)

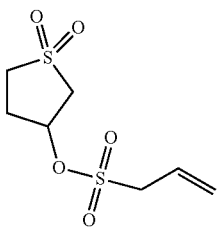
(9)

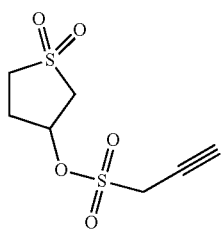
(10)

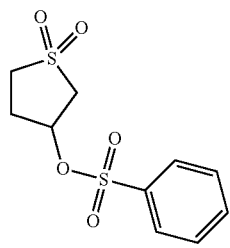
(11)

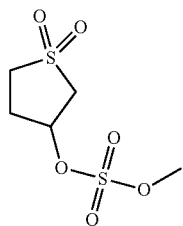
(12)

-continued

(13)
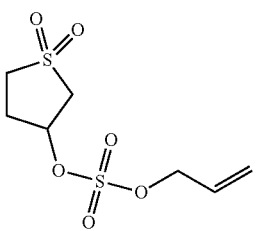

(14)
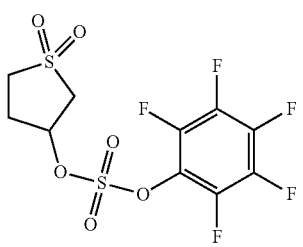

(15)
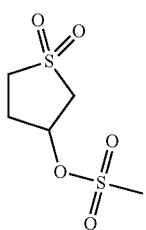

The compound of Formula (1) exhibits low LUMO energy, such that it is susceptible to electrochemical reduction. As a result, in a case of being used in a power storage device such as a non-aqueous electrolyte solution secondary battery, a non-aqueous electrolyte solution containing the compound as an additive for non-aqueous electrolyte solutions can form a stable SEI on the surface of an electrode to improve battery characteristics such as cycle characteristics, a charge/discharge capacity, and internal resistance. Further, since the compound of For (1) is stable against moisture and temperature changes, an additive for non-aqueous electrolyte solutions and a non-aqueous electrolyte solution containing these compound can be stored at room temperature for a long period of time.

The lowest unoccupied molecular orbital (LUMO) energy of the compound represented by Formula (1) may be −3.0 eV or more and may be 0.0 eV or less. If the LUMO energy is −3.0 eV or more, it can be easy to avoid formation of an SEI that exhibits high resistance on a negative electrode due to excessive decomposition of the compound. If the LUMO energy is 0.0 eV or less, it can be easy to form a more stable SEI on the surface of a negative electrode. From the same viewpoints, the LUMO energy may be −2.0 eV or more and may be −0.1 eV or less. Those skilled in the art can find a compound exhibiting LUMO energy within these numeral value ranges within a range of the compound defined by Formula (1) without excessive trials and errors.

In the present specification, the "lowest unoccupied molecular orbital (LUMO) energy" is a value calculated by the combination of PM3 that is a semi-empirical molecular orbital calculation method and B3LYP that is a density-functional theory calculation method. Specifically, the LUMO energy can be calculated using Gaussian 03 (Revision B. 03, a software manufactured by Gaussian, Inc., USA).

Those skilled in the art can synthesize the compound of Formula (1) by the combination of common reactions, using available raw materials. For example, the compound of Formula (1a), which is one of specific examples of the compound of Formula (1), can be synthesized by reacting a halide with 3-hydroxysulfolane.

The following specific examples show a case of producing the compound of Formula (1a). First, 3-hydroxysulfolane and triethylamine are dissolved in an organic solvent, then acetyl chloride is added dropwise thereto, and the mixture is stirred at room temperature for 2 hours. Thereafter, the obtained reaction product is subjected to liquid separation with water, and the oil layer is concentrated, whereby a desired compound can be obtained.

The additive for non-aqueous electrolyte solutions according to the present embodiment may include other common components such as a compound which can contribute to the formation of an SEI, in addition to the compound of Formula (1). Alternatively, the compound of Formula (1) itself can be used as the additive for non-aqueous electrolyte solutions. The additive for non-aqueous electrolyte solutions according to the present embodiment may include other common components within a range not interfering with the effect exhibited by the invention. Examples of such other common components include vinylene carbonate (VC), fluoroethylene carbonate (FEC), 1,3-propanesultone (PS), a negative electrode protecting agent, a positive electrode protecting agent, a flame retardant, and an anti-overcharging agent.

The non-aqueous electrolyte solution according to the present embodiment contains the additive for non-aqueous electrolyte solutions, a non-aqueous solvent, and an electrolyte. The content of the additive (or the compound of Formula (1)) for a non-aqueous electrolyte solution in the non-aqueous electrolyte solution may be 0.005% by mass or more and may be 10% by mass or less, with respect to the total mass of the non-aqueous electrolyte solution. If the content is 0.005% by mass or more, it becomes easy for a stable SEI to be sufficiently formed by the electrochemical reaction on the surface of an electrode. If the content is 10% by mass or less, the additive for non-aqueous electrolyte solutions can be easily dissolved in a non-aqueous solvent. Further, by preventing the content of the additive for non-aqueous electrolyte solutions from being excessively large, an increase in the viscosity of the non-aqueous electrolyte solution can be suppressed, and thus, the ion mobility can be easily secured. If the ion mobility is not sufficiently secured, the electrical conductivity or the like of the non-aqueous electrolyte solution cannot be sufficiently secured, possibly causing a problem in charge/discharge characteristics of the electricity storage device. From the same viewpoints, the content of the additive (or the compound of Formula (1)) for a non-aqueous electrolyte solution may be 0.01% by mass or more, may be 0.1% by mass or more, or may be 0.5% by mass or more. From the same viewpoints, the content of the additive (or the compound of Formula (1)) for a non-aqueous electrolyte solution may be 5% by mass or less and may be 2.0% by mass or less.

The non-aqueous electrolyte solution may include two or more additives (two or more compounds forming an SEI) for a non-aqueous electrolyte solution. In this case, the total content of the additives for a non-aqueous electrolyte solution may be 0.005% by mass or more and may be 10% by mass or less, with respect to the total mass of the non-aqueous electrolyte solution. Examples of such other additives include vinylene carbonate (VC), fluoroethylene carbonate (FEC), and 1,3-propanesultone (PS).

From the viewpoints of, for example, reducing the viscosity of the non-aqueous electrolyte solution to be obtained to a lower value, an aprotic solvent can be selected as the non-aqueous solvent. The aprotic solvent may be at least one selected from the group consisting of a cyclic carbonate, a straight-chain carbonate, an aliphatic carboxylic acid ester, a lactone, a lactam, a cyclic ether, a straight-chain ether, a sulfone, a nitrile, and a halogen derivative thereof. Among them, as the aprotic solvent, a cyclic carbonate or a straight-chain carbonate can be selected, and a combination of a cyclic carbonate and a straight-chain carbonate can also be selected.

Examples of the cyclic carbonate include ethylene carbonate, propylene carbonate, and butylene carbonate. Examples of the straight-chain carbonate include dimethyl carbonate, diethyl carbonate, and ethylmethyl carbonate. Examples of the aliphatic carboxylic acid ester include methyl acetate, ethyl acetate, methyl propionate, ethyl propionate, methyl butyrate, methyl isobutyrate, and methyl trimethylacetate. Examples of the lactone include γ-butyrolactone. Examples of the lactam include ε-caprolactam and N-methylpyrrolidone. Examples of the cyclic ether include tetrahydrofuran, 2-methyltetrahydrofuran, tetrahydropyran, and 1,3-dioxolane. Examples of the straight-chain ether include 1,2-diethoxyethane and ethoxymethoxyethane. Examples of the sulfone include sulfolane. Examples of the nitrile include acetonitrile. Examples of the halogen derivative include 4-fluoro-1,3-dioxolan-2-one, 4-chloro-1,3-dioxolan-2-one, and 4,5-difluoro-1,3-dioxolan-2-one. These non-aqueous solvents may be used alone or in combination of two or more kinds thereof. These non-aqueous solvents are particularly suitable for, for example, non-aqueous electrolyte solution secondary batteries such as a lithium ion battery, or electric double layer capacitors such as a lithium ion capacitor.

The electrolyte constituting the non-aqueous electrolyte solution may be a lithium salt which serves as an ion source of lithium ions. Among these, the electrolyte may be at least one selected from the group consisting of $LiAlCl_4$, $LiBF_4$, $LiPF_6$, $LiClO_4$, $LiAsF_6$, and $LiSbF_6$. As the electrolyte, $LiBF_4$ and/or $LiPF_6$ may be selected from the viewpoints that, for example, they have a high degree of dissociation to increase the ion conductivity of the electrolyte solution, and also have an action of suppressing deterioration of the performance of a power storage device by a long-term use due to their oxidation-reduction resistance characteristics. These electrolytes may be used alone or in combination of two or more kinds thereof. $LiBF_4$ and $LiPF_6$ can be combined with one or more cyclic carbonates and one or more straight-chain carbonates as the non-aqueous solvent. In particular, $LiBF_4$ and/or $LiPF_6$ as the electrolyte, and ethylene carbonate and diethyl carbonate as the non-aqueous solvent can also be combined.

The concentration of the electrolyte in the non-aqueous electrolyte solution may be 0.1 mol/L or more and may be 2.0 mol/L or less. If the concentration of the electrolyte is 0.1 mol/L or more, the electrical conductivity or the like of the non-aqueous electrolyte solution is easily sufficiently secured. Thus, if the concentration of the electrolyte is 0.1 mol/L or more, the electricity storage device easily obtains stable discharge characteristics and charge characteristics. If the concentration of the electrolyte is 2.0 mol/L or less, an increase in the viscosity of the non-aqueous electrolyte solution can be suppressed to particularly easily secure the ion mobility. If the ion mobility is not sufficiently secured, the electrical conductivity or the like of the electrolyte solution cannot be sufficiently secured, possibly causing a problem in charge/discharge characteristics or the like of a power storage device. From the same viewpoint, the concentration of the electrolyte may be 0.5 mol/L or more and 1.5 mol/L or less.

The electricity storage device according to the present embodiment is mainly constituted with the non-aqueous electrolyte solution, a positive electrode, and a negative electrode. Specific examples of the electricity storage device include non-aqueous electrolyte solution secondary batteries (a lithium ion battery and the like) and electric double layer capacitors (a lithium ion capacitor and the like). The non-aqueous electrolyte solution according to the present embodiment is particularly effective in applications of a lithium ion battery and a lithium ion capacitor.

FIG. 1 is a cross-sectional view schematically showing an embodiment of a power storage device. A power storage device 1 shown in FIG. 1 is a non-aqueous electrolyte solution secondary battery. The electricity storage device 1 includes a positive electrode plate 4 (positive electrode), a negative electrode plate 7 (negative electrode) facing the positive electrode plate 4, a non-aqueous electrolyte solution 8 disposed between the positive electrode plate 4 and the negative electrode plate 7, and a separator 9 provided in the non-aqueous electrolyte solution 8. The positive electrode plate 4 has a positive electrode collector 2 and a positive electrode active material layer 3 provided on the side of the non-aqueous electrolyte solution 8. The negative electrode plate 7 has a negative electrode collector 5 and a negative electrode active material layer 6 provided on the side of the non-aqueous electrolyte solution 8. As the non-aqueous electrolyte solution 8, the non-aqueous electrolyte solution according to the above-mentioned embodiment can be used. Although FIG. 1 shows a non-aqueous electrolyte solution secondary battery as the electricity storage device, the electricity storage device to which the non-aqueous electrolyte solution can be applied is not limited thereto, and it may be one of other electricity storage devices such as an electric double layer capacitor.

The positive electrode collector 2 and the negative electrode collector 5 may be a metal foil formed of metals such as aluminum, copper, nickel, and stainless steel.

The positive electrode active material layer 3 includes a positive electrode active material. The positive electrode active material may be a lithium-containing composite oxide. Specific examples of the lithium-containing composite oxide include $LiMnO_2$, $LiFeO_2$, $LiCoO_2$, $LiMn_2O_4$, $Li_2FeSiO_4$, $LiNi_{1/3}Co_{1/3}Mn_{1/3}O_2$, $LiNi_5Co_1Mn_2O_2$, and $LiFePO_4$.

The negative electrode active material layer 6 includes a negative electrode active material. The negative electrode active material may be, for example, a material capable of absorbing and releasing lithium. Examples of such a material include carbon materials such as graphite and amorphous carbon and oxide materials such as indium oxide, silicon oxide, tin oxide, zinc oxide, and lithium oxide. The negative electrode active material may be a lithium metal or a metal material capable of forming an alloy with lithium. Specific examples of the metal capable of forming an alloy with lithium include Cu, Sn, Si, Co, Mn, Fe, Sb, and Ag. A binary or ternary alloy including any of these metals and lithium can also be used as the negative electrode active material. These negative electrode active materials may be used alone or in combination of two or more kinds thereof.

The separator 9 may be a porous film formed of, for example, polyethylene, polypropylene, or fluorine resins.

Specific forms such as a shape and a thickness of the respective members constituting the electricity storage device can be appropriately set by those skilled in the art. The configuration of the electricity storage device is not limited to the embodiment of FIG. 1 and can be subjected to appropriate modifications.

EXAMPLES

The invention will be described below in more detail with reference to Examples. But the invention is not limited to these Examples.

1. Preparation of Non-aqueous Electrolyte Solution

Example 1

A mixed non-aqueous solvent was prepared by mixing ethylene carbonate (EC) and diethyl carbonate (DEC) at a compositional volume ratio of EC:DEC=30:70. $LiPF_6$ as an electrolyte was dissolved in the obtained mixed non-aqueous solvent to a concentration of 1.0 mol/L. Compound 1 shown in Table 1 as an additive for non-aqueous electrolyte solutions was added to the obtained solution to prepare a non-aqueous electrolyte solution. The content of the additive (Compound 1) for a non-aqueous electrolyte solution was set to 0.5% by mass with respect to the total mass of the non-aqueous electrolyte solution.

Example 2

A non-aqueous electrolyte solution was prepared in the same manner as in Example 1 except that the content of Compound 1 was set to 1.0% by mass.

Example 3

A non-aqueous electrolyte solution was prepared in the same manner as in Example 1 except that the additive for non-aqueous electrolyte solutions was changed from Compound 1 to Compound 2 shown Table 1, and the content thereof was set to 1.0% by mass.

Example 4

A non-aqueous electrolyte solution was prepared in the same manner as in Example 1 except that the additive for non-aqueous electrolyte solutions was changed from Compound 1 to Compound 3 shown Table 1, and the content thereof was set to 1.0% by mass.

Example 5

A non-aqueous electrolyte solution was prepared in the same manner as in Example 1 except that the additive for non-aqueous electrolyte solutions was changed from Compound 1 to Compound 4 shown Table 1, and the content thereof was set to 1.0% by mass.

Example 6

A non-aqueous electrolyte solution was prepared in the same manner as in Example 1 except that the additive for non-aqueous electrolyte solutions was changed from Compound 1 to Compound 5 shown Table 1, and the content thereof was set to 1.0% by mass.

Example 7

A non-aqueous electrolyte solution was prepared in the same manner as in Example 1 except that the additive for non-aqueous electrolyte solutions was changed from Compound 1 to Compound 6 shown Table 1, and the content thereof was set to 1.0% by mass.

Example 8

A non-aqueous electrolyte solution was prepared in the same manner as in Example 1 except that the additive for non-aqueous electrolyte solutions was changed from Compound 1 to Compound 7 shown Table 1, and the content thereof was set to 1.0% by mass.

Example 9

A non-aqueous electrolyte solution was prepared in the same manner as in Example 1 except that the additive for non-aqueous electrolyte solutions was changed from Compound 1 to Compound 8 shown Table 1, and the content thereof was set to 1.0% by mass.

Example 10

A non-aqueous electrolyte solution was prepared in the same manner as in Example 1 except that the additive for non-aqueous electrolyte solutions was changed from Compound 1 to Compound 9 shown Table 1, and the content thereof was set to 1.0% by mass.

Example 11

A non-aqueous electrolyte solution was prepared in the same manner as in Example 1 except that the additive for non-aqueous electrolyte solutions was changed from Compound 1 to Compound 10 shown Table 1, and the content thereof was set to 1.0% by mass.

Example 12

A non-aqueous electrolyte solution was prepared in the same manner as in Example 1 except that the additive for non-aqueous electrolyte solutions was changed from Compound 1 to Compound 11 shown in Table 1, and the content thereof was set to 1.0% by mass.

Comparative Example 1

A non-aqueous electrolyte solution was prepared in the same manner as in Example 1 except that Compound 1 was not added.

Comparative Example 2

A non-aqueous electrolyte solution was prepared in the same manner as in Example 1 except that the additive for non-aqueous electrolyte solutions was changed from Compound 1 to 1,3-propanesultone, and the content thereof was set to 1.0% by mass.

Comparative Example 3

A non-aqueous electrolyte solution was prepared in the same manner as in Example 1 except that the additive for non-aqueous electrolyte solutions was changed from Compound 1 to vinylene carbonate (VC), and the content thereof was set to 1.0% by mass.

Comparative Example 4

A non-aqueous electrolyte solution was prepared in the same manner as in Comparative Example 3 except that the content of vinylene carbonate (VC) was set to 2.0% by mass.

Comparative Example 5

A non-aqueous electrolyte solution was prepared in the same manner as in Example 1 except that the additive for non-aqueous electrolyte solutions was changed from Compound 1 to fluoroethylene carbonate (FEC), and the content thereof was set to 1.0% by mass.

Comparative Example 6

A non-aqueous electrolyte solution was prepared in the same manner as in Comparative Example 5 except that the content of fluoroethylene carbonate (FEC) was set to 2.0% by mass.

Comparative Example 7

A non-aqueous electrolyte solution was prepared in the same manner as in Example 1 except that the additive for non-aqueous electrolyte solutions was changed from Compound 1 to sulfolane, and the content thereof was set to 1.0% by mass.

2. Evaluation

Measurement of LUMO Energy

The LUMO (lowest unoccupied molecular orbital) energy of Compounds 1 to 11 used in Examples was determined by semi-empirical molecular orbital calculation, using a Gaussian 03 software. The calculated LUMO energy is shown in Table 1.

TABLE 1

| Compound | Compound structure | LUMO Energy (eV) |
|---|---|---|
| Compound 1 | | −0.19 |
| Compound 2 | | −0.53 |
| Compound 3 | | −0.78 |
| Compound 4 | 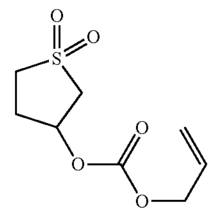 | −0.48 |
| Compound 5 | 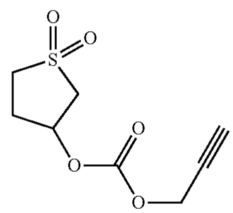 | −0.49 |
| Compound 6 | 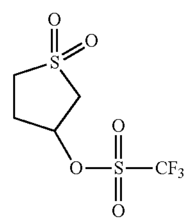 [SMILES: O=S1(=O)CCC(OS(=O)(=O)C(F)(F)F)C1] | −0.26 |
| Compound 7 | 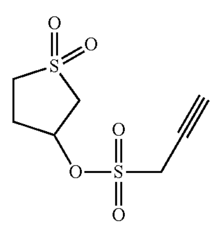 | −0.56 |
| Compound 8 | 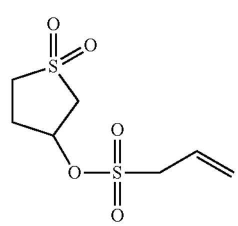 | −0.5 |
| Compound 9 | 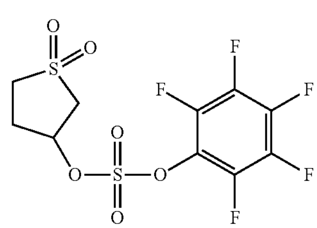 [SMILES: O=S1(=O)CCC(OS(=O)(=O)Oc2c(F)c(F)c(F)c(F)c2F)C1] | −0.76 |

TABLE 1-continued

| Compound structure | LUMO Energy (eV) |
|---|---|
| Compound 10 | −0.58 |
| Compound 11 | −0.48 |

Stability

Compounds 1 to 11 used in Examples and the fluoroethylene carbonate (FEC) used in Comparative Examples 5 and 6 were provided for a storage test for 90 days under constant temperature/constant humidity environments of a temperature of 40±2° C. and a humidity of 75±5%. The $^1$H-nuclear magnetic resonance ($^1$H-NMR) spectra of each additive for non-aqueous electrolyte solutions before and after the storage test were measured, and the stability of each compound was evaluated in accordance with the following criteria. Table 2 shows the evaluation results of the stability.

A: There was no change in the peaks of the $^1$H-NMR spectra before and after the storage test.

B: A slight change in the peaks of the $^1$H-NMR spectra before and after the storage test was found.

C: An obvious change in the peaks of the $^1$H-NMR spectra before and after the storage test was found.

TABLE 2

| Additive | Stability |
|---|---|
| Compound 1 | A |
| Compound 2 | A |
| Compound 3 | A |
| Compound 4 | A |
| Compound 5 | A |
| Compound 6 | A |
| Compound 7 | A |
| Compound 8 | A |
| Compound 9 | A |
| Compound 10 | A |
| Compound 11 | A |
| FEC | C |

As shown in Table 2, the fluoroethylene carbonate (FEC) used in Comparative Examples 5 and 6 was considered to be partially hydrolyzed and had deteriorated stability. On the other hand, Compounds 1 to 11 used in Examples showed almost no change in the peaks of the $^1$H-NMR spectra and had excellent stability.

Manufacture of Non-aqueous Electrolyte Solution Secondary Battery $LiNi_{1/3}Co_{1/3}Mn_{1/3}O_2$ as a positive electrode active material and carbon black as an electrical conductivity-imparting agent were dry-mixed. The obtained mixture was uniformly dispersed in N-methyl-2-pyrrolidone (NMP) in which polyvinylidene fluoride (PVDF) as a binder had been dissolved, thereby manufacturing a slurry. The obtained slurry was applied to both surfaces of an aluminum metal foil (square, thickness of 20 μm). The coating film was dried to remove NMP, and the whole film was pressed to obtain a positive electrode sheet having the aluminum metal foil as a positive electrode collector and a positive electrode active material layer formed on both surfaces of the foil. The ratio of the solid contents in the positive electrode active material layer of the obtained positive electrode sheet was as follows: positive electrode active material:electrical conductivity-imparting agent: PVDF=92:4:4 in terms of mass.

A commercially available graphite-coated electrode sheet (manufactured by Hohsen Corporation, trade name: ELECTRODE SHEET NEGATIVE ELECTRODE MONOLAYER) was used as a negative electrode sheet.

In each of the non-aqueous electrolyte solutions obtained in Examples and Comparative Examples, a polyethylene-made separator, a negative electrode sheet, a polyethylene-made separator, a positive electrode sheet, a polyethylene-made separator, and a negative electrode sheet were laminated in this order to manufacture a battery element. This battery element was put in a bag formed of a laminated film having aluminum (thickness: 40 μm) and resin layers coated on both sides thereof, such that the terminals of the positive electrode sheet and the negative electrode sheets protruded from the bag. Then, each of the non-aqueous electrolyte solutions obtained in Examples and Comparative Examples was poured into the bag. The bag was vacuum-sealed to obtain a sheet-shaped non-aqueous electrolyte solution secondary battery. Further, in order to increase the adhesiveness between the electrodes, the sheet-shaped non-aqueous electrolyte solution secondary battery was sandwiched between glass plates and pressurized to manufacture a non-aqueous electrolyte solution secondary battery (sheet-shaped secondary battery).

Evaluation of Discharge Capacity Retention and Internal Resistance Ratio

The obtained non-aqueous electrolyte solution secondary battery was subjected to a charge/discharge cycle test under the conditions of a charging rate of 0.3 C, a discharging rate of 0.3 C, a charge termination voltage of 4.2 V, and a discharge termination voltage of 2.5 V at 25° C. The discharge capacity retention (%) after 200 cycles and the internal resistance ratio after 200 cycles are shown in Table 3.

Here, the "discharge capacity retention (%)" after 200 cycles is a ratio (percentage) of the discharge capacity (mAh) after 200 cycles in the test with respect to the discharge capacity (mAh) after 10 cycles in the test. The "internal resistance ratio" after 200 cycles is expressed as a relative value of the resistance after 200 cycles in the test in a case where the resistance before the cycle test was taken as 1.

TABLE 3

|  | Electrolyte | Solvent | Additive | Discharge capacity retention (%) | Internal resistance ratio |
|---|---|---|---|---|---|
| Ex. 1 | LiPF$_6$ 1.0 mol/L | EC/DEC (30/70) vol % | Compound 1 0.5% by mass | 79 | 1.69 |
| Ex. 2 | LiPF$_6$ 1.0 mol/L | EC/DEC (30/70) vol % | Compound 1 1.0% by mass | 83 | 1.65 |
| Ex. 3 | LiPF$_6$ 1.0 mol/L | EC/DEC (30/70) vol % | Compound 2 1.0% by mass | 83 | 1.60 |
| Ex. 4 | LiPF$_6$ 1.0 mol/L | EC/DEC (30/70) vol % | Compound 3 1.0% by mass | 85 | 1.62 |
| Ex. 5 | LiPF$_6$ 1.0 mol/L | EC/DEC (30/70) vol % | Compound 4 1.0% by mass | 88 | 1.59 |
| Ex. 6 | LiPF$_6$ 1.0 mol/L | EC/DEC (30/70) vol % | Compound 5 1.0% by mass | 90 | 1.59 |
| Ex. 7 | LiPF$_6$ 1.0 mol/L | EC/DEC (30/70) vol % | Compound 6 1.0% by mass | 87 | 1.41 |
| Ex. 8 | LiPF$_6$ 1.0 mol/L | EC/DEC (30/70) vol % | Compound 7 1.0% by mass | 89 | 1.52 |
| Ex. 9 | LiPF$_6$ 1.0 mol/L | EC/DEC (30/70) vol % | Compound 8 1.0% by mass | 89 | 1.55 |
| Ex. 10 | LiPF$_6$ 1.0 mol/L | EC/DEC (30/70) vol % | Compound 9 1.0% by mass | 88 | 1.44 |
| Ex. 11 | LiPF$_6$ 1.0 mol/L | EC/DEC (30/70) vol % | Compound 10 1.0% by mass | 90 | 1.47 |
| Ex. 12 | LiPF$_6$ 1.0 mol/L | EC/DEC (30/70) vol % | Compound 11 1.0% by mass | 88 | 1.48 |
| Comp. Ex. 1 | LiPF$_6$ 1.0 mol/L | EC/DEC (30/70) vol % | None | 68 | 1.83 |
| Comp. Ex. 2 | LiPF$_6$ 1.0 mol/L | EC/DEC (30/70) vol % | 1,3-Propanesultone 1.0% by mass | 71 | 1.68 |
| Comp. Ex. 3 | LiPF$_6$ 1.0 mol/L | EC/DEC (30/70) vol % | VC 1.0% by mass | 78 | 1.59 |
| Comp. Ex. 4 | LiPF$_6$ 1.0 mol/L | EC/DEC (30/70) vol % | VC 2.0% by mass | 77 | 1.67 |
| Comp. Ex. 5 | LiPF$_6$ 1.0 mol/L | EC/DEC (30/70) vol % | FEC 1.0% by mass | 84 | 1.66 |
| Comp. Ex. 6 | LiPF$_6$ 1.0 mol/L | EC/DEC (30/70) vol % | FEC 2.0% by mass | 85 | 1.67 |
| Comp. Ex. 7 | LiPF$_6$ 1.0 mol/L | EC/DEC (30/70) vol % | Sulfolane 1.0% by mass | 76 | 1.77 |

Measurement of Amount of Gas Generated

In addition to the batteries used in the cycle test, a non-aqueous electrolyte solution secondary batteries including each of the electrolyte solutions of Examples and Comparative Examples were prepared. Three cycles of an operation in which the battery was charged to 4.2 V at a current corresponding to 0.2 C, and then discharged to 3 V at a current corresponding to 0.2 C were carried out at 25° C. to stabilize the battery. Subsequently, the battery was charged again to 4.2 V at a charging rate of 0.3 C, and then stored at a high temperature of 60° C. for 168 hours. Thereafter, the battery was cooled to room temperature, the volume of the battery was measured by the Archimedes' method, and the amount of gas generated was determined from a change in the volume before and after the storage.

TABLE 4

|  | Electrolyte | Solvent | Additive | Amount of gas generated (cm$^3$) |
|---|---|---|---|---|
| Example 13 | LiPF$_6$ 1.0 mol/L | EC/DEC (30/70) vol % | Compound1 1.0% by mass | 0.51 |
| Example 14 | LiPF$_6$ 1.0 mol/L | EC/DEC (30/70) vol % | Compound 2 1.0% by mass | 0.45 |
| Example 15 | LiPF$_6$ 1.0 mol/L | EC/DEC (30/70) vol % | Compound 3 1.0% by mass | 0.39 |
| Example 16 | LiPF$_6$ 1.0 mol/L | EC/DEC (30/70) vol % | Compound 4 1.0% by mass | 0.42 |
| Example 17 | LiPF$_6$ 1.0 mol/L | EC/DEC (30/70) vol % | Compound 5 1.0% by mass | 0.41 |
| Example 18 | LiPF6 1.0 mol/L | EC/DEC (30/70) vol % | Compound 6 1.0% by mass | 0.37 |
| Example 19 | LiPF$_6$ 1.0 mol/L | EC/DEC (30/70) vol % | Compound 7 1.0% by mass | 0.35 |
| Example 20 | LiPF$_6$ 1.0 mol/L | EC/DEC (30/70) vol % | Compound 8 1.0% by mass | 0.34 |
| Example 21 | LiPF$_6$ 1.0 mol/L | EC/DEC (30/70) vol % | Compound 9 1.0% by mass | 0.32 |
| Example 22 | LiPF$_6$ 1.0 mol/L | EC/DEC (30/70) vol % | Compound 10 1.0% by mass | 0.30 |
| Example 23 | LiPF$_6$ 1.0 mol/L | EC/DEC (30/70) vol % | Compound 11 1.0% by mass | 0.33 |
| Comparative Example 8 | LiPF$_6$ 1.0 mol/L | EC/DEC (30/70) vol % | None | 0.54 |
| Comparative Example 9 | LiPF$_6$ 1.0 mol/L | EC/DEC (30/70) vol % | FEC 1.0% by mass | 0.58 |
| Comparative Example 10 | LiPF$_6$ 1.0 mol/L | EC/DEC (30/70) vol % | VC 1.0% by mass | 0.59 |

As shown in Tables 3 and 4, it can be seen that the non-aqueous electrolyte solution secondary battery using the non-aqueous electrolyte solution of each of Examples, including Compounds 1 to 11 which are the compounds of Formula (1), are excellent in both of the discharge capacity retention in the cycle test and the suppression of gas generation caused by the charging, as compared with the non-aqueous electrolyte solution secondary batteries using the non-aqueous electrolyte solutions of Comparative Examples. This strongly suggests that in a case where the compound of Formula (1) is used in a non-aqueous electrolyte solution secondary battery, an SET which is stable for charge/discharge cycles and high-temperature storage is formed. In addition, it was found that the compound of Formula (1) is excellent in that the increase in the internal resistance due to the charge/discharge cycles is small.

REFERENCE SIGNS LIST

1: Power storage device (non-aqueous electrolyte solution secondary battery),
2: Positive electrode collector,
3: Positive electrode active material layer,
4: Positive electrode plate,
5: Negative electrode collector,
6: Negative electrode active material layer,
7: Negative electrode plate,
8: Non-aqueous electrolyte solution,
9: Separator.

The invention claimed is:

1. An additive for non-aqueous electrolyte solutions, comprising
a compound represented by Formula (1a),

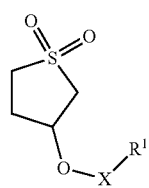

(1a)

wherein, in Formula (1a), X represents a sulfonyl group, and
$R^1$ represents an alkyl group having 2 to 4 carbon atoms or an alkyl group having 1 to 4 carbon atoms which is substituted with a fluorine atom, an alkenyl group having 2 to 4 carbon atoms which may be substituted with a fluorine atom, an alkynyl group having 2 to 4 carbon atoms which may be substituted with a fluorine atom, an aryl group which may be substituted with a fluorine atom, an alkoxy group having 1 to 4 carbon atoms which may be substituted with a fluorine atom, an alkenyloxy group having 2 to 4 carbon atoms which may be substituted with a fluorine atom, an alkynyloxy group having 2 to 4 carbon atoms which may be substituted with a fluorine atom, or an aryloxy group which may be substituted with a fluorine atom, wherein one or more of hydrogen atoms bonded to carbon atoms in each of the groups of $R^1$ may be substituted with a fluorine atom.

2. A non-aqueous electrolyte solution comprising:
an additive for non-aqueous electrolyte solutions
a non-aqueous solvent; and
an electrolyte, wherein the additive includes:
a compound represented by Formula (1a),

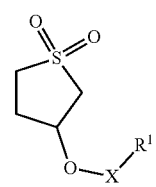

(1a)

in Formula (1a), X represents a carbonyl group or a sulfonyl group, wherein:
when X represents a carbonyl group, $R^1$ represents an alkyl group having 1 to 4 carbon atoms which is substituted with a fluorine atom, an alkenyl group having 2 to 4 carbon atoms which may be substituted with a fluorine atom, an alkynyl group having 2 to 4 carbon atoms which may be substituted with a fluorine atom, an aryl group which may be substituted with a fluorine atom, an alkoxy group having 1 to 4 carbon atoms which may be substituted with a fluorine atom, an alkenyloxy group having 2 to 4 carbon atoms which may be substituted with a fluorine atom, an alkynyloxy group having 2 to 4 carbon atoms which may be substituted with a fluorine atom, or an aryloxy group which may be substituted with a fluorine atom, and
when X represents a sulfonyl group, $R^1$ represents an alkyl group having 1 to 4 carbon atoms which may be substituted with a fluorine atom, an alkenyl group having 2 to 4 carbon atoms which may be substituted with a fluorine atom, an alkynyl group having 2 to 4 carbon atoms which may be substituted with a fluorine atom, an aryl group which may be substituted with a fluorine atom, an alkoxy group having 1 to 4 carbon atoms which may be substituted with a fluorine atom, an alkenyloxy group having 2 to 4 carbon atoms which may be substituted with a fluorine atom, an alkynyloxy group having 2 to 4 carbon atoms which may be substituted with a fluorine atom, or an aryloxy group which may be substituted with a fluorine atom, wherein
one or more of hydrogen atoms bonded to carbon atoms in each of the groups of $R^1$ may be substituted with a fluorine atom.

3. The non-aqueous electrolyte solution according to claim 2,
wherein the non-aqueous solvent includes a cyclic carbonate and a straight-chain carbonate.

4. The non-aqueous electrolyte solution according to claim 2, wherein the electrolyte includes a lithium salt.

5. A power storage device comprising:
the non-aqueous electrolyte solution according to claim 2;
a positive electrode; and
a negative electrode.

6. A lithium ion battery comprising:
the non-aqueous electrolyte solution according to claim 2;
a positive electrode; and
a negative electrode.

7. A lithium ion capacitor comprising:
the non-aqueous electrolyte solution according to claim 2;
a positive electrode; and
a negative electrode.

* * * * *